United States Patent [19]

Pfister

[11] 3,993,669

[45] Nov. 23, 1976

[54] MONO- AND DISUBSTITUTED 1,4-BENZOPYRONE-6-CARBOXYLIC ACIDS AND DERIVATIVES THEREOF

[75] Inventor: Jürg R. Pfister, Los Altos, Calif.

[73] Assignee: Syntex (U.S.A.) Inc., Palo Alto, Calif.

[22] Filed: Apr. 17, 1975

[21] Appl. No.: 569,023

Related U.S. Application Data

[63] Continuation-in-part of Ser. No. 476,751, June 5, 1974, abandoned.

[52] U.S. Cl............................ 260/345.2; 260/515 A; 260/520 E; 424/283
[51] Int. Cl.$^2$........................................ C07D 311/02
[58] Field of Search.................................. 260/345.2

[56] References Cited

UNITED STATES PATENTS

| 3,433,805 | 3/1969 | Kramer et al. | 260/345.2 |
|---|---|---|---|
| 3,770,802 | 11/1973 | Sianesi | 260/345.2 |
| 3,862,143 | 1/1975 | Klutchko et al. | 260/345.2 |
| 3,862,175 | 1/1975 | Fitzmaurice et al. | 260/345.2 |
| 3,872,108 | 3/1975 | Ukyo et al. | 260/345.2 |
| 3,872,130 | 3/1975 | Kreighbaum et al. | 260/289 R |

FOREIGN PATENTS OR APPLICATIONS

| 823,875 | 4/1975 | Belgium | 260/345.2 |

OTHER PUBLICATIONS

Shah et al., Current Sci. (India), 22, 306–307 (1953).
Save et al., J. Indian Chem. Soc., 49, 25 (1972).
Save et al., (I), J. Indian Chem. Soc., 48, 675 (1971).

Primary Examiner—James O. Thomas, Jr.
Assistant Examiner—Nicky Chan
Attorney, Agent, or Firm—Alan M. Krubiner; William B. Walker

[57] ABSTRACT

Novel C-2 mono- and C-2,3-disubstituted 1,4-benzopyrone-6-carboxylic acids and derivatives thereof which are useful as bronchiodilators. Methods for preparing these compounds are also disclosed.

13 Claims, No Drawings

MONO- AND DISUBSTITUTED 1.4-BENZOPYRONE-6-CARBOXYLIC ACIDS AND DERIVATIVES THEREOF

This case is a continuation-in-part of application Ser. No. 476,751, filed June 5, 1974, now abandoned.

SUMMARY

The present invention is directed to novel mono and disubstituted 1.4-benzopyrone-6-carboxylic acids, their preparation and to compositions containing and methods utilizing these compounds as the essential ingredient in the treatment of symptoms associated with bronchioconstriction.

In a first aspect, the present invention relates to novel C-2 mono and C-2,3-disubstituted 1.4-benzopyrone-6-carboxylic acids of the formula:

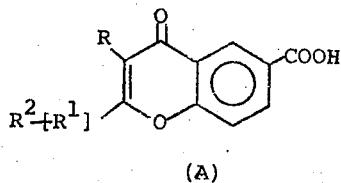

(A)

and the pharmaceutically acceptable, non-toxic salts and esters thereof,
wherein:
R is hydrogen, lower alkyl, lower alkoxy, or hydroxy;
$R^1$ is phenyl, or naphthyl; and
$R^2$ is hydrogen, hydroxy, lower alkoxy, or halo; provided that when $R^1$ is phenyl and
 a. R is hydrogen, $R^2$ is not hydrogen, 4'-lower alkoxy or halo;
 b. R is lower alkyl, $R^2$ is not hydrogen or halo;
 c. R is lower alkoxy containing more than 2 carbon atoms, $R^2$ is not hydrogen, 3'-alkoxy or 4'-fluoro;
 d. R is hydroxy, $R^2$ is not hydrogen or 4'-halo.

A preferred subclass of compounds falling within the class defined by Formula (A) are those compounds of the formula:

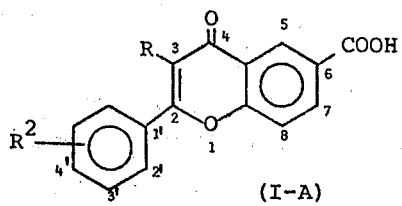

(I-A)

and the pharmaceutically acceptable, non-toxic salts and esters thereof, wherein R and $R^2$ are as previously defined subject to the above provisos.

Within the subclass defined by Formula (I-A), a first preferred group of compounds are those wherein R and $R^2$ are lower alkoxy subject to proviso (c) above. Particularly preferred compounds in this group include 2-(2'-methoxyphenyl)-3-methoxy-1.4-benzopyrone-6-carboxylic acid, 23 '-methoxyphenyl)-3-methoxy-1.4-benzopyrone-6-carboxylic acid, 2-(4'-methoxyphenyl)-3-methoxy-1.4-benzopyrone-6-carboxylic acid, 2-(4'-methoxyphenyl)-3-ethoxy-1.4-benzopyrone-6-carboxylic acid, 2-(4'-methoxyphenyl)-3-isopropoxy-1.4-benzopyrone-6-carboxylic acid and the pharmaceuticaly acceptable non-toxic salts and esters thereof.

A second preferred group of compounds within the subclass defined by Formula (I-A) are those wherein R is lower alkoxy and $R^2$ is halo subject to proviso (c) above. Particularly preferred compounds within this group are those wherein R is lower alkoxy containing 1 to 2 carbon atoms and $R^2$ is halo, e.g., 2-(4'-fluorophenyl)-3-methoxy-1.4-benzopyrone-6-carboxylic acid and the pharmaceutically acceptable, nontoxic salts and esters thereof; and compounds wherein R is lower alkoxy containing 3 to 6 carbon atoms and $R^2$ is halo other than at the 4'-position.

A third preferred group of compounds within the subclass defined by Formula (I-A) are those wherein R and $R^2$ are hydroxy, e.g. 2-(3'-hydroxyphenyl)-3-hydroxy-1.4-benzopyrone-6-carboxylic acid and the pharmaceutically acceptable nontoxic salts and esters thereof.

The compounds of the present invention are smooth muscle relaxants, e.g. bronchiodilators, and are therefore useful in the treatment of conditions in which such agents may be indicated, as for instance in the treatment of bronchial asthma and hay fever.

Accordingly, the present invention in a second aspect is directed to a method useful for relieving symptoms associated with bronchioconstriction, which method comprises administering an effective amount of a compound selected from those represented by Formula (A) and the pharmaceutically acceptable non-toxic salts and esters thereof; or a pharmaceutically acceptable non-toxic composition incorporating said salts or esters as the essential ingredient.

The present invention in a third aspect, is directed to pharmaceutical compositions useful for inhibiting the effects of bronchioconstriction, which compositions comprise an effective amount of a compound selected from those represented by Formula (A) and the pharmaceutically acceptable non-toxic salts and esters thereof, in admixture with a pharmaceutically acceptable non-toxic carrier.

In practicing the method of the present invention, an effective amount of a compound of the present invention or pharmaceutical composition thereof, is administered via one of several acceptable methods known in the art, either singly or in combination with another compound or compounds of the present invention or other pharmaceutical agents. Thus, these compounds and compositions may be administered orally, topically, parenterally, or by inhalation and in the form of either solid, liquid, or gaseous dosages. More specifically, certain compounds of the instant invention are active bronchiodilators when administered via areosol and certain compounds of the instant invention are active bronchiodilators when administered parenterally. The administration can be conducted in single unit dosage form with continuous therapy or in single dose therapy ad libitum. In the preferred embodiments, the method of the present invention is practiced when relief of symptoms is specifically required, or, perhaps, imminent; however, the method hereof is also usefully practiced as continuous or prophylacetic treatment.

In view of the foregoing as well as consideration of the degree or severity of the condition being treated, age of subject, and so forth, the effective dosage in accordance herewith can vary over a wide range. Generally, an effective amount ranges from about 0.005 to about 200 mg. per kg. of body weight per day and preferably from about .1 to about 100 mg. per kg. of body weight per day. In alternate terms, an effective amount in accordance herewith generally ranges from about 7 to about 7000 mg. per day per subject. The compounds can be administered in unit or divided dosage forms.

Suitable pharmaceutical carriers for the preparation of the compositions of the present invention can be solids, liquids, or gases. Thus, the compositions can take the form of tablets, pills, capsules, powders, sustained release formulations, solutions, suspensions, aerosols, and the like. The carriers can be selected from the various oils including those of petroleum, animal, vegetable, or synthetic origin, for example, peanut oil, soybean oil, mineral oil, sesame oil, and the like. Water, saline, aqueous dextrose, and glycols are preferred liquid carriers, particularly for injectable solutions. Suitable pharmaceutical excipients include starch, cellulose, talc, glucose, lactose, sucrose, gelatin, malt, rice, flour, chalk, silica gel, magnesium stearate, sodium stearate, glyceryl monostearate, sodium chloride, dried skim milk, glycerol, propylene glycol, water, ethanol, and the like.

For inhalation administration, the compounds can, for example, be administered as an aerosol comprising the compound(s) in an inert propellant together with a cosolvent (e.g. ethanol) and optional preservatives and buffering agents. Additional general information concerning the inhalation administration of aerosols can be had by reference to U.S. Pat. Nos. 2,969,691 and 3,095,355.

Suitable pharmaceutical carriers and their formulation are described in "Remingtons Pharmaceutical Sciences" by E. W. Martin. The compositions of the present invention will, in any event, contain an effective amount of the active compound together with a suitable pharmaceutical carrier.

The present invention, in a further aspect, is directed to a method for the preparation of compounds of Formula (A) according to the following reaction sequence:

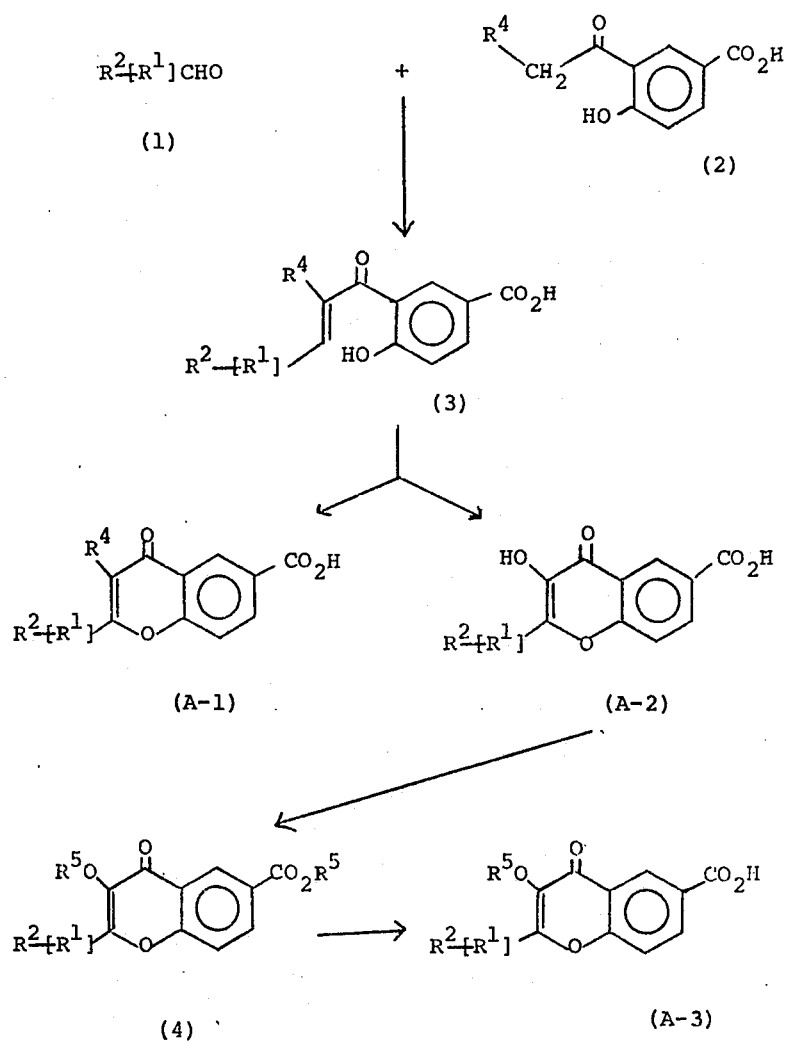

wherein $R^1$ and $R^2$ are as previously defined, $R^4$ is hydrogen or lower alkyl and $R^5$ is lower alkyl.

With reference to the above reaction sequence, an aldehyde (1) is condensed with a 3-acyl-4-hydroxybenzoic acid (2) in the presence of dilute base, such as aqueous potassium hydroxide in ethanol at a temperature of 5° to 25° C. for a period of 18 to 24 hours to yield an $\alpha,\beta$-unsaturated ketone (3).

The α,β-unsaturated ketone compound (3) is then treated with bromine to yield the corresponding dibromo compound (not shown). The bromination reaction is preferably conducted in acetic acid solution at a temperature of 5° to 25° C. for a period of 16 to 20 hours. Thereafter, the dibromo product is dehydrohalogenated to yield a C-2 mono or C-2,3-disubstituted 1.4-benzopyrone-6-carboxylic acid (A-1). ). The preferred procedure for effecting dehydrohalogenation comprises treating the dibromo product with aqueous potassium hydroxide in ethanol at a temperature of 10° to 40° C. for a period of 2 to 6 hours.

Alternatively, when R⁴ is hydrogen, alkaline hydrogen peroxide oxidation of the α,β-unsaturated ketone (3) yields a 2-substituted-3-hydroxy-1.4-benzopyrone-6-carboxylic acid (A-2). The peroxide oxidation is preferbly conducted in the presence of aqueous sodium hydroxide in ethanol at a temperature of 0° to 20° C. for a period of 12 to 15 hours.

The 2-substituted 3-hydroxy acid compound (A-2) is then treated with the desired lower alkyl halide in the presence of potassium carbonate to yield a 2-substituted-3 -alkoxy-1.4-benzopyrone-6-carboxylate (4). This reaction is carried out in a solvent such as dimethylformamide at a temperature of 20° to 60° C. for a period of 6 to 15 hours.

Thereafter, the thus prepared ester (4) is base hydrolyzed to give the corresponding 2-substituted-3-alkoxy-1.4-benzopyrone-6-carboxylic acid (A-3). The base hydrolysis conditions can be employed conventionally in the art. Generally, the hydrolysis reaction is conducted using an alkali metal hydroxide at about 50° to 90° C. for a period of 15 minutes to 1 hour. The reaction is preferably conducted in the presence of an insert, organic solvent such as those normally employed in chemical reactions of this type, e.g. aqueous alkanol solutions.

Starting compounds in the present invention are available or can be prepared by processes known per se. Thus, the 3-acyl-4-hydroxybenzoic acid starting compounds (2) are conveniently prepared by treating 4-hydroxybenzoic acid with an excess of an acyl halide of the formula

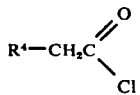

wherein R⁴ is hydrogen, methyl, ethyl, isopropyl and so forth, to give the corresponding 4-acyloxybenzoic acid. This latter compound is subjected to a Fries rearrangement by heating with aluminum chloride to yield the corresponding 3-acyl-4-hydroxybenzoic acid starting compound (2).

The acid esters of the 1.4-benzopyrone-6-carboxylic acids are prepared by treatment of the acid with an ethercal diazoalkane such as diazomethane and diazoethane or with the desired lower alkyl halide in the presence of lithium carbonate at room temperature or with the desired lower alkanol in the presence of a trace of sulfuric acid at reflux. The glycerol esters are prepared by treating the acid with thionyl chloride followed by treatment with a suitably protected glycerine derivative (e.g., solketal) in pyridine, and hydrolyzing the protecting group of the ester thus formed with dilute acid.

The salts of the 1.4-benzopyrone-6-carboxylic acids hereof are prepared by treating the corresponding acid with a pharmaceutically acceptable base. Representative salts derived from such pharmaceutically acceptable bases include the sodium, potassium, lithium, ammonium, calcium, magnesium, ferrous, ferric, zinc, manganous, aluminum, manganic, trimethylamine, triethylamine, tripropylamine, β-(diethylamino) etanol, triethanolamine, arginine, lysine, histidine, N-ethylpiperidine, hydrabamine, choline, betaine, ethylenediamine, glucosamine, methyl glucamine, theobromine, purine, piperazine, piperidine, polyamine resins, caffeine, and procaine salts. The reaction is conducted in an aqueous solution, alone or in combination with an inert, water miscible organic solvent, at a temperature of from 0 ° to about 100° C., preferably at room temperature. Typical inert, water miscible organic solvents include methanol, ethanol, isopropanol, butanol, acetone, dioxane, or tetrahydrofuran. When divalent metal salts are prepared, such as the calcium salts or magnesium salts, the free acid starting material is treated with about ½ molar equivalent of pharmaceutically acceptable base. When the aluminum salts of the acids are prepared, about ⅓ molar equivalent of the pharmaceutically acceptable base is employed.

In the preferred embodiment of the present invention, the calcium salts and magnesium salts of the acids are prepared by treating the corresponding sodium or potassium salts with at least one molar equivalent of calcium chloride or magnesium chloride, respectively, in an aqueous solution, alone or in combination with an inert water miscible organic solvent, at a temperature of from about 20° to about 100° C.

In the preferred embodiment of the present invention, the aluminum salts of the acids are prepared by treating the acids with at least ⅓ molar equivalent of an aluminum alkoxide, such as aluminum triethoxide, aluminum tripropoxide, and the like, in a hydrocarbon solvent, such as benzene, xylene, cyclohexane, and the like at a temperature of from about 20° C. to about 115° C.

The terms "lower alkyl" and "lower alkoxy" as used herein are inclusive of moieties containing from 1 to 6 carbon atoms, for example methyl, ethyl, propyl, isopropyl, butyl, isobutyl, tert. butyl, pentyl, isopentyl and the like.

The term "halo" as used herein is inclusive of chloro, bromo, and fluoro.

The terms "pharmaceutically acceptable, non-toxic esters, and salts," as used herein refer to alkyl or glycerol esters or salts as defined above.

EXAMPLE I 5-carboxy-2-hydroxyphenyl-2'-methoxy-styryl ketone

A mixture of 10 g. of 3-acetyl-4-hydroxy-benzoic acid, 10.2 g. of 2-methoxybenzaldehyde, 120 ml. of 40% aqueous potassium hydroxide and 240 ml. of ethanol is stirred at 25° C. for 22 hours. The solution is then poured into excess 1N hydrochloric acid and the precipitate which forms is filtered, washed with water and dried under vacuum at 70° C.. The product is crystallized from a mixture of tetrahydrofuran and ethanol to yield 5-carboxy-2-hydroxyphenyl-2'-methoxy-styryl ketone.

EXAMPLE 2

2-(2'-methoxyphenyl)-1.4-benzopyrone-6-carboxylic acid 5-carboxy-2-hydroxyphenyl-2'-methoxy-styryl ketone (6.2g.) is suspended in 200 ml. of acetic acid containing 2 ml. of bromine. After stirring for 18 hours at 25° C., 500 ml. of a 1% aqueous sodium bisulfate solution is added to the reaction mixture and the precipitate which forms is filtered and washed with water. The precipitate is then added to 400 ml. of a 1:1 mixture of water and ethanol containing 5 g. of potassium hydroxide. After stirring for 5 hours at 25° C. the solution is acidified with 1 N hydrochloric acid and the precipitate isolated by suction filtration. Crystallization of the product from acetic acid yields 2-(2'- methoxyphenyl)-1.4-benzopyrone-6- carboxylic acid.

EXAMPLE 3

2-substituted-1.4-benzopyrone-6-carboxylic acids, and 2,3-disubstituted-1.4-benzopyrone-6-carboxylic acids Repeating the procedures of Examples 1 and 2, but substituting the aldehydes listed in Column V and the 3-acyl-4-hydroxybenzoic acids listed in Column VI as starting compounds in Example 1 is productive of the 2-substituted- and 2,3-disubstituted-1.4-benzopyrone-6-carboxylic acids listed in column VII.

V

2-, 3- and 4-hydroxybenzaldehyde
2- , 3- and 4-methoxybenzaldehyde
2- and 4-ethoxybenzaldehyde
2-, 3- and 4-bromobenzaldehyde
2-, 3- and 4-chlorobenzaldehyde
2-, 3- and 4-fluorobenzaldehyde
1-naphthylaldehyde
2-naphthylaldehyde
2-hydroxy-1-naphthylaldehyde
2-methoxy-1-naphthylaldehyde
4-methoxy-1-naphthylaldehyde

VI 3-acetyl-4-hydroxybenzoic acid
3-propionyl-4-hydroxybenzoic acid
3-butyryl-4-hydroxybenzoic acid
3-isovalerylbenzoic acid

VII 2-(2'-hydroxyphenyl)-1.4-benzopyrone-6-carboxylic acid,
2 -(3'-hydroxyphenyl)-1.4-benzopyrone-6-carboxylic acid,
2-(4'-hydroxyphenyl)-1.4-benzopyrone-6-carboxylic acid,
2-(3'-methoxyphenyl)-1.4-benzopyrone-6-carboxylic acid,
2-(2'-ethoxyphenyl)-1.4-benzopyrone-6-carboxylic acid,
2-(1'-naphthyl)-1.4-benzopyrone-6-carboxylic acid,
2-(2'-naphthyl)-1.4-benzopyrone-6-carboxylic acid,
2-(2'-hydroxy-1'-naphthyl)-1.4-benzopyrone-6-carboxylic acid,
2-(2'-methoxy-1'-naphthyl)-1.4-benzopyrone-6-carboxylic acid,
2-(4'-methoxy-1'-naphthyl)-1.4-benzopyrone-6-carboxylic acid,
2-(2'-hydroxyphenyl)3-methyl-1.4-benzopyrone-6-carboxylic acid,
2-(3'-hydroxyphenyl)-3-methyl-1.4-benzopyrone-6-carboxylic acid,
2- (4'-hydroxyphenyl)-3-methyl-1.4-benzopyrone-6-carboxylic acid,
2-(2'-methoxyphenyl)-3-methyl-1.4-benzopyrone-6-carboxylic acid,
2-(3'-methoxyphenyl)-3-methyl-1.4-benzopyrone-6-carboxylic acid,
2-(3'-methoxyphenyl)-3-methyl-1.4-benzopyrone-6-carboxylic acid,
2-(2'- ethoxyphenyl)-3-methyl-1.4-benzopyrone-6-carboxylic acid,
2-(4'-ethoxyphenyl)-3-methyl-1.4-benzopyrone-6-carboxylic acid,
2-(1'-naphthyl)-3-methyl-1.4-benzopyrone-6-carboxylic acid,
2-(2'-naphthyl)-3-methyl-1.4-benzopyrone-6-carboxylic acid,
2-(2'methoxy-1'-naphthyl)-3-methyl-1.4-benzopyrone-6-carboxylic acid,
2-(4'-methoxy1'-naphthyl)-3-methyl-1.4-benzopyrone-6-carboxylic acid,
2-(2'-hydroxyphenyl)-3-ethyl-1.4-benzopyrone-6-carboxylic acid,
2-(3'-hydroxyphenyl)-3-ethyl-1.4-benzopyrone-6-carboxylic acid,
2-(4'-hydroxyphenyl)-3-ethyl-1.4-benzopyrone-6-carboxylic acid,
2-(2'-methoxyphenyl)-3-ethyl-1.4-benzopyrone-6-carboxylic acid,
3-(2'-methoxyphenyl)--3-ethyl-1.4-benzopyrone-6-carboxylic acid,
2-(4'-methoxyphenyl)-3-ethyl-1.4-benzopyrone-6-carboxylic acid,
2-(2'-ethoxyphenyl)-3-ethyl-1.4-benzopyrone-6-carboxylic acid,
2-(4'-ethoxyphenyl)-3-ethyl-1.4-benzopyrone-6-carboxylic acid,
2-(1'-naphthyl)-3-ethyl-1.4-benzopyrone-6-carboxylic acid,
2-(2'-naphthyl)-3-ethyl-1.4-benzopyrone-6-carboxylic acid,
2-(2'-hydroxy-1'-naphthyl)-3-ethyl-1.4-benzopyrone-6-carboxylic acid,
2-(2'-methoxy -1'-naphthyl)-3-ethyl-1.4-benzopyrone-6-carboxylic acid,
2-(4'-methoxy-1'-naphthyl)-3-ethyl-1.4-benzopyrone-6-carboxylic acid,
2-(2'-hydroxyphenyl)-3-n-propyl-1.4-benzopyrone-6-carboxylic acid,
2-(3'-hydroxyphenyl)-3-n-propyl-1.4-benzopyrone-6-carboxylic acid,
2-(4'-hydroxyphenyl)-3-n-propyl-1.4-benzopyrone-6-carboxylic acid,
2-(2'-methoxyphenyl)-3-n-propyl-1.4-benzopyrone-6-carboxylic acid,
2-(3'- methoxyphenyl)-3-n-propyl-1.4-benzopyrone-6 carboxylic acid,
2-(4'-methoxyphenyl)-3-n-propyl-1.4-benzopyrone-6-carboxylic acid,
2-(2'-ethoxyphenyl)-3-n-propyl-1.4-benzopyrone-6-carboxylic acid,
2-(4'-ethoxyphenyl)-3-n-propyl-1.4-benzopyrone-6-carboxylic acid,
2-(1'-naphthyl)-3-propyl-1.4-benzopyrone-6-carboxylic acid, 2-(2'-naphthyl)-3-n-propyl-1.4-benzopyrone-6-carboxylic acid,
2-(2'-hydroxy-1'-naphthyl)-3-n-propyl-1.4-benzopyrone-6-carboxylic acid,
2-(2'-methoxy-1'-naphthyl)-3-n-propyl-1.4-benzopyrone-6-carboxylic acid,
2-(4'-methoxy-1'-naphthyl)-3-n-propyl-1.4-benzopyrone-6-carboxylic acid,
2-(2'-hydroxyphenyl)-3-isopropyl-1.4-benzopyrone-6-carboxylic acid,
2-(3'-hydroxyphenyl)-3-isopropyl-1.4-benzopyrone-6-carboxylic acid,
2-(4'-hydroxyphenyl)-3-isopropyl-1.4-benzopyrone-6-carboxylic acid,
2-(2'-methoxyphenyl)-3-isopropyl-1.4-benzopyrone-6-carboxylic acid,
2-(3'-methoxyphenyl)-3-isopropyl-1.4-benzopyrone-6-carboxylic acid,
2-(4'-methoxyphenyl)-3-isopropyl-1.4-benzopyrone-6-carboxylic acid,
2-(2'-ethoxyphenyl)-3-isopropyl-1.4-benzopyrone-6-carboxylic acid,
2-(4'-ethoxyphenyl)-3-isopropyl-1.4-benzopyrone-6-carboxylic acid,
2-(2'-naphthyl)-3-isopropyl-1.4-benzopyrone-6-carboxylic acid,
2-(2'-naphthyl)-3-isopropyl-1.4-benzopyrone-6-carboxylic acid,
2-(2'-hydroxy-1'-naphthyl)-3-isopropyl-1.4-benzopyrone-6-carboxylic acid,
2-(2'-methoxy-1'-naphthyl)-3-isopropyl-1.4-benzopyrone-6-carboxylic acid, and
2-(4'-methoxy-1'-naphthyl)-3-isopropyl-1.4-benzoyprone-6-carboxylic acid.

EXAMPLE 4

2-(2'-methoxyphenyl)-3-hydroxy-1.4-benzopyrone-6-carboxylic acid

A mixture of 10.9 g. of 5-carboxy-2-hydroxyphenyl-2'-methoxy-styryl ketone, 66 ml. of 16.5% hydrogen peroxide, 275 ml. of 5% aqueous sodium hydroxide and 275 ml. of ethanol is stirred at 0° C. for 3 hours and then 25° C. for 24 hours. Excess 1 N HCl is then added to the solution and the precipitate which forms is filtered, washed with water and crystallized from acetic acid to yield 2-(2'-methoxyphenyl)-3-hydroxy-1.4-benzopyrone-6-carboxylic acid.

EXAMPLE 5

2-(2'-methoxyphenyl)-3-isopropyl-1.4-benzopyrone-6-carboxylic acid a. A mixture of 2-(2'-methoxyphenyl)-3-hydroxy-1.4-benzopyrone-6-carboxylic acid, 12 ml. of 2-bromopropane, 12 g. of potassium carbonate and 60 ml. of dimethylformamide is stirred at 60° C. for 5 hours. The reaction mixture is then poured into 300 ml. of 2 N hydrochloric acid containing 5 g. of sodium bisulfite. The organic layer is extracted with chloroform and the chloroform layer evaporated to dryness to yield isopropyl 2-(2'-methoxyphenyl)-3-isopropoxy-1.4-benzopyrone-6-carboxylate.

b. 2.45 g. of the above ester is refluxed with 80 ml. of water and ethanol (1:1) containing 500 mg. of potassium hydroxide. After 30 minutes the solution is acidified with 1 N hydrochloric acid. The precipitate which forms is filtered, washed with water and crystallized from ethanol to yield 2-(2'-methoxyphenyl)-3-isopropoxy-1.4-benzopyrone-6-carboxylic acid, m.p. 203° C.

Replacing 2-bromopropane in the above procedure with alternate alkyl halides yields the corresponding 2-substituted-3-alkoxy-1.4-benzopyrone-6-carboxylic acids, e.g., 2-(2'-methoxyphenyl)-3-methoxy-1.4-benzopyrone-6-carboxylic acid, m.p. 229° C., 2-(2'-methoxyphenyl)-3-ethoxy-1.4-benzopyrone-6-carboxylic acid, 2-(2'-methoxyphenyl)-3-n-butoxy-1.4-benzopyrone-6-carboxylic acid and so forth.

EXAMPLE 6

2-substituted-3-hydroxy-1.4-benzopyrone-6-carboxylic acids

Repeating the procedure of Example 1 with selected aldehydes listed in Column V of Example 3, followed by treatment of the products according to the procedure of Example 4 yields the corresponding:

2-(2'-hydroxyphenyl)-3-hydroxy-1.4-benzopyrone-6-carboxylic acid,
2-(3'-hydroxyphenyl)-3-hydroxy-1.4-benzopyrone-6-carboxylic acid, m.p. 325° C.,
2-(4'-hydroxyphenyl)-3-hydroxy-1.4-benzopyrone-6-carboxylic acid, m.p. 348° C.,
2-(3'-methoxyphenyl)-3-hydroxy-1.4-benzopyrone-6-carboxylic acid,
2-(4'-methoxyphenyl)-3-hydroxy-1.4-benzopyrone-6-carboxylic acid, m.p. >350° C. (decomp.),
2-(2'-ethoxyphenyl)-3-hydroxy-1.4-benzopyrone-6-carboxylic acid,
2-(4'-ethoxyphenyl)-3-hydroxy-1.4-benzopyrone-6-carboxylic acid,
2-(2'-bromophenyl)-3-hydroxy-1.4-benzopyrone-6-carboxylic acid, m.p. 285°–287° C.,
2-(3'-bromophenyl)-3-hydroxy-1.4-benzopyrone-6-carboxylic acid,
2-(2'-chlorophenyl)-3-hydroxy-1.4-benzopyrone-6-carboxylic acid,
2-(3'-chlorophenyl)-3-hydroxy-1.4-benzopyrone-6-carboxylic acid,
2-(2'-fluorophenyl)-3-hydroxy-1.4-benzopyrone-6-carboxylic acid,
2-(3'-fluorophenyl)-3-hydroxy-1.4-benzopyrone-6-carboxylic acid,
2-(1'-naphthyl)-3-hydroxy-1.4-benzopyrone-6-carboxylic acid,
2-(2'-naphthyl)-3-hydroxy-1.4-benzopyrone-6-carboxylic acid,
2-(2'-hydroxy-1'-naphthyl)-3-hydroxy-1.4-benzopyrone-6-carboxylic acid,
2-(2'-methoxy-1'-naphthyl)-3-hydroxy-1.4-benzopyrone-6-carboxylic acid, and
2-(4'-methoxy-1'-naphthyl)-3-hydroxy-1.4-benzopyrone-6-carboxylic acid.

EXAMPLE 7

2-substituted-3-alkoxy-1.4-benzopyrone-6-carboxylic acid

Repeating the procedure of Example 5 with selected products of Example 6 yields the corresponding:

2-(2'-hydroxyphenyl)-3-isopropoxy-1.4-benzopyrone-6-carboxylic acid,
2-(3'-hydroxyphenyl)-3-isopropoxy-1.4-benzopyrone-6-carboxylic acid, 2-(4'-hydroxyphenyl)-3-isopropoxy-1.4-benzopyrone-6-carboxylic acid,
2-(4'-methoxyphenyl)-3-isopropoxy-1.4-benzopyrone-6-carboxylic acid, m.p. 262°–264° C.,
2-(2'-ethoxyphenyl)-3isopropoxy-1.4-benzopyrone-6-carboxylic acid,
2-(2'-bromophenyl)-3-isopropoxy-1.4-benzopyrone-6-carboxylic acid,
2-(3'-bromophenyl)-3-isopropoxy-1.4-benzopyrone-6-carboxylic acid,
2-(4'-bromophenyl)-3-isopropoxy-1.4-benzopyrone-6-carboxylic acid,
2-(2'-chlorophenyl)-3-isopropoxy-1.4-benzopyrone-6-carboxylic acid,
2-(3'-chlorophenyl)-3-isopropoxy-1.4-benzopyrone-6-carboxylic acid,
2-(4'-chlorophenyl)-3-isopropoxy-1.4-benzopyrone-6-carboxylic acid,
2-(2'-fluorophenyl)-3-isopropoxy-1.4-benzopyrone-6-carboxylic acid,
2-(3'-fluorophenyl)-3-isopropoxy-1.4-benzopyrone-6-carboxylic acid,
2-(1'-naphthyl)-3-isopropoxy-1.4-benzopyrone-6-carboxylic acid,
2-(2'-methoxy-1'-naphthyl)-3-isopropoxy-1.4-benzopyrone-6-carboxylic acid, and
2-(4'-methoxy-1'-naphthyl)-3-isopropoxy-1.4-benzopyrone-6-carboxylic acid.

In like manner, other 2-substituted 3-alkoxy-1.4-benzopyrone-6-carboxylic acids are prepared, for example:
2-phenyl-3-methoxy-1.4-benzopyrone-6-carboxylic acid, m.p. 254° C.,
2-(2'-hydroxyphenyl)-3-methoxy-1.4-benzopyrone-6-carboxylic acid,
2-(3'-hydroxyphenyl)-3-methoxy-1.4-benzopyrone-6-carboxylic acid,
2-(4'-hydroxyphenyl)-3-methoxy-1.4-benzopyrone-6-carboxylic acid,
2-(3'-methoxyphenyl)-3-methoxy-1.4-benzopyrone-6-carboxylic acid, m.p. 213° C.,
2-(4'-methoxyphenyl)-3-methoxy-1.4-benzopyrone-6-carboxylic acid, m.p. 252° C.,
2-(2'-ethoxyphenyl)-3-methoxy-1.4-benzopyrone-6-carboxylic acid,
2-(4'-ethoxyphenyl)-3-methoxy-1.4-benzopyrone-6-carboxylic acid,
2-(2'-bromophenyl)-3-methoxy-1.4-benzopyrone-6-carboxylic acid, m.p. 204°–205° C.,
2-(3'-bromophenyl)-3-methoxy-1.4-benzopyrone-6-carboxylic acid,
2-(4'-bromophenyl)-3-methoxy-1.4-benzopyrone-6-carboxylic acid,
2-(2'-chlorophenyl)-3-methoxy-1.4-benzopyrone-6-carboxylic acid,
2-(3'-chlorophenyl)-3-methoxy-1.4-benzopyrone-6-carboxylic acid,
2-(4'-chlorophenyl)-3-methoxy-1.4-benzopyrone-6-carboxylic acid, m.p. >300° C. (decomp.),
2-(2'-fluorophenyl)-3-methoxy-1.4-benzopyrone-6-carboxylic acid,
2-(3'-fluorophenyl)-3-methoxy-1.4-benzopyrone-6-carboxylic acid,
2-(4'-fluorophenyl)-3-methoxy-1.4-benzopyrone-6-carboxylic acid, m.p. 275°–276° C.,
2-(1'-naphthyl)-3-methoxy-1.4-benzopyrone-6-carboxylic acid,
2-(2'-methoxy-1'-naphthyl)-3-methoxy-1.4-benzopyrone-6-carboxylic acid,
2-(4'-methoxy-1'-naphthyl)-3-methoxy-1.4-benzopyrone-6-carboxylic acid,
2-phenyl-2-ethoxy-1.4-benzopyrone-6-carboxylic acid,
2-(2'-hydroxyphenyl)-3-ethoxy-1.4-benzopyrone-6-carboxylic acid,
2-(2'-hydroxyphenyl)-3-ethoxy-1.4-benzopyrone-6-carboxylic acid,
2-(3'-hydroxyphenyl)-3-ethoxy-1.4-benzopyrone-6-carboxylic acid,
2-(4'-hydroxyphenyl)-3-ethoxy-1.4-benzopyrone-6-carboxylic acid,
2-(3'-methoxyphenyl)-3-ethoxy-1.4-benzopyrone-6-carboxylic acid, m.p. 186° C.,
2-(4'-methoxyphenyl)-3-ethoxy-1.4-benzopyrone-6-carboxylic acid, m.p. 233° C.,
2-(2'-ethoxyphenyl)-3-ethoxy-1.4-benzopyrone-6-carboxylic acid,
2-(4'-ethoxyphenyl)-3-ethoxy-1.4-benzopyrone-6-carboxylic acid,
2-(2'-bromophenyl)-3-ethoxy-1.4-benzopyrone-6-carboxylic acid,
2-(3'-bromophenyl)-3-ethoxy-1.4-benzopyrone-6-carboxylic acid,
2-(4'-bromophenyl)-3-ethoxy-1.4-benzopyrone-6-carboxylic acid,
2-(2'-chlorophenyl)-3-ethoxy-1.4-benzopyrone-6-carboxylic acid,
2-(3'-chlorophenyl)-3-ethoxy-1.4-benzopyrone-6-carboxylic acid,
2-(4'-chlorophenyl)-3-ethoxy-1.4-benzopyrone-6-carboxylic acid,
2-(2'-fluorophenyl)-3-ethoxy-1.4-benzopyrone-6-carboxylic acid,
2-(3'-fluorophenyl)-3-ethoxy-1.4-benzopyrone-6-carboxylic acid, and
2-(4'-fluorophenyl)-3-ethoxy-1.4-benzopyrone-6-carboxylic acid and also the corresponding 2-substituted 3-n-butoxy- and 3-isobutoxy-1.4-benzopyrone-6-carboxylic acid.

EXAMPLE 8

1.4-benzopyrone-6-carboxylic acid esters

A mixture of 4.8 g. of 2-(4'-methoxyphenyl)-3-methoxy-1.4-benzopyrone-6-carboxylic acid, 10 g. of methyl iodide, and 10 g. of lithium carbonate in 75 ml. of dimethylformamide is stirred at room temperature for a period of 18 hours. Thereafter, the reaction mixture is poured into dilute hydrochloric acid-ice and the resultant precipitate is filtered off and washed to yield methyl 2-(4'-methoxyphenyl)-3-methoxy-1.4-benzopyrone-6-carboxylate, m.p. 178° C.

Repeating the procedure using alternate lower alkyl halides is productive of the corresponding lower alkyl acid esters, e.g. ethyl 2-(4'-methoxyphenyl)-3-methoxy-1.4-benzopyrone-6-carboxylate, n-propyl 2-(4'-methoxyphenyl)-3-methoxy-1.4-benzopyrone-6-carboxylate, isopropyl 2-(4'-methoxyphenyl)-3-methoxy-1.4-benzopyrone-6-carboxylate, isobutyl 2-(4'-methoxyphenyl)-3-methoxy-1.4-benzopyrone-6-carboxylate, sec-butyl 2-(4'-methoxyphenyl)-3-methoxy-1.4-benzopyrone-6-carboxylate, t-butyl 2-(4'-methoxyphenyl)-3-methoxy-1.4-benzopyrone-6-carboxylate, n-pentyl 2-(4'-methoxyphenyl)-3-methoxy-1.4-benzopyrone-6-carboxylate, and so forth.

In like manner, the acid esters of other C-2 mono- and C-2,3-disubstituted 1.4-benzopyrone-6-carboxylic acids are prepared, for example, methyl 2-(4'-methoxyphenyl)-3-hydroxy-1.4-benzopyrone-6-carboxylate, m.p. 213°–215° C.,
methyl 2-phenyl-3-methoxy-1.4-benzopyrone-6-carboxylate, m.p. 133° C.,
methyl 2-(2'-methoxyphenyl)-3-methoxy-1.4-benzopyrone-6-carboxylate,
methyl 2-(3'-methoxyphenyl)-3-methoxy-1.4-benzopyrone-6-carboxylate, m.p. 113°–117° C.,
methyl 2-(4'-chlorophenyl)-3-methoxy-1.4-benzopyrone-6-carboxylate, m.p. 179°–180° C.,
methyl 2-(4'-fluorophenyl)-3-methoxy-1.4-benzopyrone-6-carboxylate, m.p. 157° C.,
ethyl 2-(3'-methoxyphenyl)-3-ethoxy-1.4-benzopyrone-6-carboxylate,
ethyl 2-(4'-methoxyphenyl)-3-ethoxy-1.4-benzopyrone-6-carboxylate, m.p. 135° C.,
isopropyl 2-(3'-hydroxyphenyl)-3-isopropoxy-1.4-benzopyrone-6-carboxylate, m.p. 165° C.,
isopropyl 2-(4'-hydroxyphenyl)-3-isopropoxy-1.4-benzopyrone-6-carboxylate, m.p. 212°–213° C.,
isopropyl 2-(2'-methoxyphenyl)-3-isopropoxy-1.4-benzopyrone-6-carboxylate, and
isopropyl 2-(4'-methoxyphenyl)-3-isopropoxy-1.4-benzopyrone-6-carboxylate, m.p. 112° C.

EXAMPLE 9

1.4-benzopyrone-6-carboxylic acid salts

To a solution of 11 g. of 2-(4'-chlorophenyl)-3-methoxy-1.4-benzopyrone-6-carboxylic acid in 200 ml. of ethanol is added the theoretical amount of sodium hydroxide dissolved in 200 ml. of 90% ethanol. The reaction mixture is then concentrated in vacuum to give sodium 2-(4'-chlorophenyl)-3-methoxy-1.4-benzopyrone-6-carboxylate, m.p. >300° C. (decomp.).

The lithium and potassium salts of 2-(4'-chlorophenyl)-3-methoxy-1.4-benzopyrone-6-carboxylic acid are prepared in a similar manner.

Treating the thus obtained sodium or potassium salt with an appropriate metal salt reagent, e.g. calcium chloride, manganese chloride, and so forth, is productive of other acid salts, e.g. calcium 2-(4'-chlorophenyl)-3-methoxy-1.4-benzopyrone-6-carboxylate, manganese 2-(4'-chlorophenyl)-3-methoxy-1.4-benzopyrone-6-carboxylate, aluminum 2-(4'-chlorophenyl)-3-methoxy-1.4-benzopyrone-6-carboxylate, ferrous 2-(4'-chlorophenyl)-3-methoxy-1.4-benzopyrone-6-carboxylate, ferric 2-(4'-chlorophenyl)-3-methoxy-1.4-benzopyrone-6-carboxylate, zinc 2-(4'-chlorophenyl)-3-methoxy-1.4-benzopyrone-6-carboxylate, and so forth.

In like manner, the acid salts of other C-2 mono- and C-2,3-disubstituted 1.4-benzopyrone-6-carboxylic acids are prepared, e.g., sodium 2-(4'-methoxyphenyl)-3-hydroxy-1.4-benzopyrone-6-carboxylate, m.p. >350° C. (decomp.), potassium 2-(4'-methoxyphenyl)-3-hydroxy-1.4-benzopyrone-6-carboxylate, m.p. >340° C. (decomp.), sodium 2-(4'-chlorophenyl)-3-methoxy-1.4-benzopyrone-6-carboxylate, m.p. >300° C. (decomp.), and so forth.

Preparation of the ammonium salts is accomplished as follows:

to a mixture of 50 ml. of concentrated aqueous ammonia in 500 ml. of methanol is added 22 g. of 2-(3'-methoxyphenyl)-3-isopropoxy-1.4-benzopyrone-6-carboxylic acid. The resultant mixture is stirred for 2 hours and is then evaporated to dryness to yield the ammonium salt of 2-(3'-methoxyphenyl)-3-isopropoxy-1.4-benzopyrone-6-carboxylic acid.

EXAMPLE 10

A tablet composition is prepared from the following ingredients in the indicated proportions:

| Component | Percent by weight |
|---|---|
| a 1.4-benzopyrone-6-carboxylic acid compound hereof | 35 |
| polyvinylpyrrolidone | 3 |
| starch | 5.7 |
| lactose | 56 |
| magnesium stearate | 0.3 |
| granulating fluid | |

The starch is added to a small amount of granulating fluid, e.g. purified water, and heated at 70° C. until a paste is formed. The starch paste is then added to a mixture of the 1.4-benzopyrone-6-carboxylic acid compound, lactose and polyvinylpyrrolidone. The wet granulation is thoroughly mixed and passed through a suitable screen. Thereafter, the granulation is dried in the oven until loss of drying is less than 2%. The dry granulation is then screened through a suitable screen, mixed thoroughly with magnesium stearate, and tabulated with a conventional tablet press.

EXAMPLE 11

The following illustrates a test procedure for selected compounds of the instant invention:

Female guinea pigs weighing 400–500 g. are anesthetized with urethane (1 g./Kg., administered I.P.) and both the trachea and the jugular vein are cannulated. The trachial cannula (plastic tube) is attached to a Harvard ventilator and pressure transducer to measure respiratory resistance. The jugular cannula (22 gage needle) permits I.V. administration of histamine and the bronchiodilator test compound.

A standard histamine challenge (5μg.), causing bronchio-constriction, is given to determine the animal's sensitivity to histamine. Five minutes later the test compound is administered at a dosage of 25 mg./G. Pig.

The mean % inhibition of the histamine response is then determined for each test compound and compared with that of the standard, Aminophylline (Theophylline ethylenediamine).

The data presented in the following table illustrates the bronchiodilating potency exhibited by selected compounds of the instant invention.

| Compound | Mean % Inhib. of Hist. Response[1] |
|---|---|
| Standard (Aminophylline) | 68 |
| sodium 2-(4'-methoxyphenyl)-3-isopropoxy 1.4-benzopyrone-6-carboxylate | 75 |
| sodium 2-(3'-methoxyphenyl)-3-methoxy- 1.4-benzopyrone-6-carboxylate | 76 |
| sodium 2-(4'-methoxyphenyl)-3-methoxy- 1.4-benzopyrone-6-carboxylate | 72 |
| sodium 2-(4'-fluorophenyl)-3-methoxy- 1.4-benzopyrone-6-carboxylate | 75 |
| sodium 2-(3'-hydroxyphenyl)-3-hydroxy-1.4-benzopyrone-6-carboxylate | 100 |

-continued

| Compound | Mean % Inhib. of Hist. Response[1] |
|---|---|
| sodium 2-(4'-methoxyphenyl)-3-ethoxy-1.4-benzopyrone-6-carboxylate | 88 |
| sodium 2-(4'-hydroxyphenyl)-3-hydroxy-1.4-benzopyrone-6-carboxylate | 78 |
| sodium 2-phenyl-3-methoxy-1.4-benzopyrone-6-carboxylate | 98 |
| sodium 2-(2'-methoxyphenyl)-3-methoxy-1.4-benzopyrone-6-carboxylate. | 72 |

[1]Each compound is tested in two Guinea pigs.

Inhibition of histamine induced bronchioconstriction in guinea pigs is regarded as representative of inhibition of human bronchioconstriction which occurs during episodes of bronchial asthma. Protection against histamine induced bronchioconstriction is regarded as representative of human bronchopulmonary activity including bronchiodilator activity.

Subjects suffering from bronchopulmonary disorders, such as asthma, are studied as to severity of bronchospasm and changes in severity by observable and measurable changes in expiratory function. Such measurements include quantitation of expiratory pulmonary air flow, measurable by such instruments as a peak flow meter, and comparison of pulmonary volumes before and after treatment with the subject compounds hereof, as measured by spirometric and/or pletysmographic methods. Subjective relief of the symptoms upon administration of the compounds hereof is evidenced by improvements of dyspnea, wheezing, cough and expectorated sputum.

What is claimed is:
1. A compound of the formula

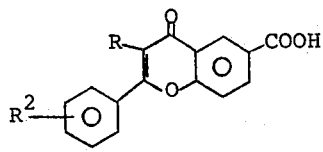

and the pharmaceutically acceptable non-toxic salts and esters thereof, wherein:
R is lower alkoxy; and
$R^2$ is hydrogen, hydroxy, lower alkoxy or halo; provided that when R is lower alkoxy containing more than 2 carbon atoms $R^2$ is not hydrogen, 3'-lower alkoxy or 4'-fluoro.

2. A compound of claim 1 wherein R is methoxy.
3. The compound of claim 2 wherein $R^2$ is 2'-methoxy; 2-(2'-methoxyphenyl)-3-methoxy-1.4-benzopyrone-6-carboxylic acid.
4. The compound of claim 2 wherein $R^2$ is 3'-methoxy; 2-(3'-methoxyphenyl)-3-methoxy-1.4-benzopyrone-6-carboxylic acid.
5. The compound of claim 2 wherein $R^2$ is 4'-methoxy; 2-(4'-methoxyphenyl)-3-methoxy-1.4-benzopyrone-6-carboxylic acid.
6. The compound of claim 2 wherein $R^2$ is 4'-fluoro; 2-(4'-fluorophenyl)-3-methoxy-1.4-benzopyrone-6-carboxylic acid.
7. The compound of claim 2 wherein $R^2$ is hydrogen; 2-phenyl-3-methoxy-1.4-benzopyrone-6-carboxylic acid.
8. A compound of claim 1 wherein R is isopropoxy.
9. The compound of claim 8 wherein $R^2$ is 4'-methoxy; 2-(4'-methoxyphenyl)-3-isopropoxy-1.4-benzopyrone-6-carboxylic acid.
10. The compound of claim 8 wherein $R^2$ is 2'-methoxy; 2-(2'-methoxyphenyl)-3-isopropoxy-1.4-benzopyrone-6-carboxylic acid.
11. A compound of claim 1 wherein R is ethoxy.
12. The compound of claim 11 wherein $R^2$ is 4'-methoxy; 2-(4'-methoxyphenyl)-3-ethoxy-1.4-benzopyrone-6-carboxylic acid.
13. The compound of claim 11 wherein $R^2$ is 3'-methoxy; 2-(3'-methoxyphenyl)-3-ethoxy-1.4-benzopyrone-6-carboxylic acid.

* * * * *

UNITED STATES PATENT AND TRADEMARK OFFICE
CERTIFICATE OF CORRECTION

PATENT NO. : 3,993,669
DATED : November 23, 1976
INVENTOR(S) : JURG R. PFISTER

It is certified that error appears in the above-identified patent and that said Letters Patent are hereby corrected as shown below:

Column 1, line 61, "23'-methoxyphenyl)" should read -- 2-(3'-methoxyphenyl) --. Column 5, line 36, "insert" should read -- inert --. Column 5, line 60, "ethercal" should read -- ethereal --. Column 8, line 11, "2-(3'-methoxyphenyl)" should read -- 2-(4'-methoxyphenyl) --. Column 8, between lines 20 and 21, the following compound should appear -- 2-(2'hydroxy-1'-naphthyl)-3-methyl-1.4-benzopyrone-6-carboxylic acid --. Column 8, line 23, "2-(4'-methoxyl'-naphthyl)" should read -- 2-(4'-methoxy-1'-naphthyl) --. Column 8, line 33, "3-(2'-methoxyphenyl)" should read -- 2-(3'-methoxyphenyl) --. Column 8, line 67, "-3-propyl-" should read -- 3-n-propyl --. Column 9, line 25, "2-(2'-naphthyl)" should read -- 2-(1'-naphthyl) --.

Signed and Sealed this

Twenty-sixth Day of April 1977

[SEAL]

Attest:

RUTH C. MASON
Attesting Officer

C. MARSHALL DANN
Commissioner of Patents and Trademarks